United States Patent [19]
Underwood et al.

[11] Patent Number: 5,530,168
[45] Date of Patent: Jun. 25, 1996

[54] PROCESS FOR THE SYNTHESIS OF A $C_2+$ ALIPHATIC ALCOHOL IN A SLURRY REACTOR COMPRISING AN IN-SITU CATALYST IMPREGNATION STEP

[75] Inventors: Richard P. Underwood; Bernard A. Toseland, both of Allentown; Thomas A. Dahl, Lansford; Janet F. Hugo, Kempton, all of Pa.

[73] Assignee: Air Products and Chemicals, Inc., Allentown, Pa.

[21] Appl. No.: 317,053

[22] Filed: Oct. 3, 1994

[51] Int. Cl.$^6$ ................................................ C07C 27/20
[52] U.S. Cl. ................................................. 568/909
[58] Field of Search ....................................... 568/909

[56] References Cited

U.S. PATENT DOCUMENTS

| | | | |
|---|---|---|---|
| 2,671,103 | 3/1954 | Kölbel, et al. | 260/449.6 |
| 4,598,061 | 7/1986 | Schneider, et al. | 502/303 |

FOREIGN PATENT DOCUMENTS

| | | |
|---|---|---|
| 353920A | 2/1990 | European Pat. Off. . |
| 448019 | 9/1991 | European Pat. Off. . |
| 3616519 | 11/1986 | Germany . |
| 126434 | 8/1982 | Japan . |
| 708744 | 5/1954 | United Kingdom . |

OTHER PUBLICATIONS

Smith and Anderson, "The Higher Alcohol Synthesis Over Promoted Cu/ZnO Catalysts", The Canadian Journal of Chemical Engineering, vol. 61, Feb. 1983, p. 40).

Nunan, et al, "Higher Alcohol and Oxygenate Synthesis over Cesium–Doped Cu/ZnO Catalysts", Journal of Catalysts, vol. 116, pp. 195–221, 1989.

R. P. Underwood, Topical Report, Task 3.2 and Task 3.3, U.S. Doe Contract No. DE–AC22–90PC89865, Dec. 1989–Feb. 1993.

P. Chaumette, et al. "Evolution of Alcohol Synthesis Catalysts Under Syngas", Ind. Eng. Chem. Res., vol. 33, pp. 1460–1467, 1994.

Frame and Galla, "Fischer–Tropsch Iron Catalyst Development", Proceedings of the US Doe Contractors Review Mtg., pp. 911–942, Sep. 1993).

*Primary Examiner*—Paul J. Killos
*Attorney, Agent, or Firm*—Robert J. Wolff

[57] ABSTRACT

A process is set forth for the synthesis of a $C_2+$ aliphatic alcohol from hydrogen and carbon oxides in the presence of a copper-based catalyst which has been impregnated with an alkali metal compound. The process differs from the prior art in that the catalyst is impregnated with the alkali metal compound in the same slurry reactor which is used for reacting the hydrogen and carbon oxides. By contrast, in the prior art $C_2+$ aliphatic alcohol synthesis, impregnation of the copper-based catalyst with the alkali metal compound is accomplished by a separate step in a separate vessel. By eliminating this separate step, the present invention realizes a savings in processing and equipment costs.

5 Claims, No Drawings

5,530,168

PROCESS FOR THE SYNTHESIS OF A $C_{2+}$ ALIPHATIC ALCOHOL IN A SLURRY REACTOR COMPRISING AN IN-SITU CATALYST IMPREGNATION STEP

This invention was made under DOE Contract Number DE-AC22-91PC90018 and is subject to government rights arising therefrom.

FIELD OF THE INVENTION

The present invention relates to a process for the synthesis of a $C_2+$ aliphatic alcohol from hydrogen and carbon oxides in a slurry reactor and more particularly to a method of catalyst impregnation for such process.

BACKGROUND OF THE INVENTION

Synthesis gas, mixtures of carbon oxides and hydrogen, can be catalytically converted to a variety of organic compounds. Of particular interest in the industry is the selective synthesis of aliphatic alcohols containing 2 or greater carbon atoms (i.e. "$C_2+$" aliphatic alcohols). These compounds have a variety of chemical uses and have been shown to have beneficial properties when added to gasoline. Of particular interest is the production of branched primary alcohols such as isobutanol, which can be dehydrated selectively to isobutylene, a key chemical intermediate.

Processes for the production of mixtures of methanol and higher alcohols from synthesis gas are taught in the art. These processes are largely based on synthesis gas conversion in the presence of a heterogeneous catalyst in a packed bed reactor. However, because synthesis gas conversion to higher alcohols is highly exothermic, the use of a slurry reactor is advantageous. In a slurry reactor, a heterogeneous catalyst, in the powder from, is suspended in a liquid medium. The intimate contact of the liquid medium with the catalyst provides a more effective means of removing the heat of reaction from the catalyst. This feature allows isothermal reactor operation at higher synthesis conversion per reactor pass than that possible in a packed bed reactor. Isothermality enables good control of reaction selectivity while protecting the catalyst from damage by local overheating.

A variety of catalysts have been developed for the synthesis of mixtures of alcohols from synthesis gas. Generally, these catalysts consist of mixed metals and/or metal oxides, or metal sulfides. Since most of these catalysts tend to produce methanol as the dominant alcohol from the "$C_1$" based feedstock, selectivity to $C_{2+}$ alcohols has been a key technical challenge. It is taught in the art that selectivity to $C_{2+}$ alcohols, particularly branched isomers, is enhanced by the inclusion of an alkali metal from group 1A of the periodic table in the catalyst formulation. Moreover, since selectivity to $C_{2+}$ alcohols is often maximized for a specific alkali content, the catalysts are often treated with a specific quantity of alkali in a controlled manner. Doping of the catalyst with alkali is usually done in a separate production step by impregnation/promotion with a solution of an alkali salt, followed by drying and, in some cases, calcination.

The objective of the present invention is to provide a simpler, more efficient method of producing an alkalized catalyst for the synthesis of $C_{2+}$ aliphatic alcohols, and more particularly isobutanol, when the catalyst is used in a slurry reactor.

The state-of-the-art catalysts for the synthesis of mixtures of alcohols, with high selectivity to $C_{2+}$ aliphatic alcohols, are mixed metals and/or metal oxides or metal sulfides which have been promoted with alkali metal. One class of these catalysts, based on copper and zinc oxide, have been shown to catalyze the synthesis of methanol and higher alcohols at high yield. Moreover, these catalysts have been shown to have a high selectivity to branched alcohols, like isobutanol, and a relatively low yield of paraffinic hydrocarbons, which are common undesirable byproducts.

Generally, copper and zinc oxide-based catalysts are produced by co-precipitation of copper, zinc, and optionally, other metals from solution by a base (commonly an alkali compound). Washing, drying and calcination of the precipitate produces the mixed oxide form. The dried and calcined catalyst is then impregnated with a solution of an alkali metal compound which contains the desired quantity of alkali, then dried and often calcined again. This procedure deposits a controlled quantity of alkali onto the catalyst surface. The catalyst is converted to the active form, which contains reduced copper, for synthesis gas conversion by reduction using a hydrogen-containing gas.

U.S. Pat. No. 4,598,061 by Schneider et al. describes a catalyst for the synthesis of methanol and higher alcohols which contains copper oxide, zinc oxide, aluminum oxide, and an alkali metal carbonate or oxide. This catalyst is formed by precipitation of copper and zinc from solution, by an alkali compound, in the presence of colloidally dispersed aluminum hydroxide. The precipitate is washed and calcined, then impregnated with an alkali metal compound and dried again. The preferred quantity of alkali metal is $13-130 \times 10^{-6}$ gram atom per gram of copper oxide/zinc oxide/aluminum oxide precursor.

Smith and Anderson (The Canadian Journal of Chemical Engineering, Volume 61, February 1983) describe a Cu/ZnO catalyst which, when promoted with potassium carbonate, yields more higher alcohols, including isobutanol, than the unpromoted version. Promotion of the Cu/ZnO substrate was done by impregnation with an aqueous solution of $K_2CO_3$. The isobutanol selectivity was maximized at 0.5 wt % $K_2CO_3$.

Nunan, et al. (Journal of Catalysis, Vol. 116, pp. 195–221, 1989) describe a cesium-promoted Cu/ZnO catalyst for the selective synthesis of higher alcohols from synthesis gas. This catalyst was formed by calcination of a copper and zinc hydroxycarbonate precursor, followed by impregnation with an aqueous solution of cesium formate (CsOOCH). The optimum catalysts, in terms of $C_{2+}$ alcohols yield, contained 0.3–0.5 mol % CsOOCH.

The above catalyst examples were used in a packed bed reactor for synthesis gas conversion. References to the selective synthesis of higher alcohols; using a slurry reactor are limited, but the following examples are worth noting.

European Patent Application EP-353920-A describes a slurry reactor based process for the production of mixed alcohols, with emphasis on the production of $C_2$–$C_6$ alcohols. The catalyst used was a potassium-promoted cobalt and molybdenum on an alumina support. Promotion with potassium was done by impregnation with an aqueous solution of an alkali salt.

R. P. Underwood (Topical Report, Task 3.2 and 3.3, U.S. DOE Contract No. DE-AC22-90PC89865, December 1989–February 1993) describes slurry phase synthesis of methanol and higher alcohols from synthesis gas. A $Cu/ZnO/Al_2O_3$ methanol synthesis catalyst, which had been promoted with cesium, was used together with mineral oil in a stirred autoclave. Promotion by cesium was done by impregnation of the $Cu/ZnO/Al_2O_3$ substrate with aqueous cesium formate, followed by drying and calcination.

Chaumette, et al. (industrial and Engineering Chemistry Research, Vol. 33, pp. 1460–1467, 1994) describe the use of alkali-promoted Cu/Co/Zn/Al based higher alcohols synthesis catalysts in a slurry reactor. Alkalization of the catalysts was done either during the precipitation step or by impregnation of the calcined precipitate.

A distinguishing feature of the above examples, which are representative of the art, is that the catalysts were promoted with alkali metal compounds by a separate impregnation step. The impregnation step involves treating the catalyst with a known quantity of a solution of an alkali compound, followed by removal of the solute by drying. In all cases, alkalization of the catalyst is production step which is done outside of the reactor used by synthesis gas conversion.

Alkalization of a catalyst in the same slurry reactor which is used for synthesis gas conversion is not taught in the art for catalysts for the synthesis of higher alcohols from synthesis gas. However, in situ alkalization is taught in the art for Fischer-Tropsch catalysts, which are used for the production of paraffinic hydrocarbons from synthesis gas.

U.S. Pat. No. 2,671,103 by Kolbel et al. pertains to a slurry reactor process for the synthesis of paraffinic hydrocarbons from synthesis gas. In the subject process, an alkali-promoted catalyst (Fe, Co, Ni, or Ru-based) is suspended in a hydrocarbon oil product. The alkali promoter enhances the selectivity to $C_{3+}$ hydrocarbons. To compensate for the loss in catalyst activity with time, catalyst is withdrawn from the reactor and fresh catalyst is added. With the fresh catalyst, a predetermined quantity of alkali is also added to make up for alkali lost in removing slurry from the reactor. The following compounds of sodium and potassium are mentioned as suitable alkali compounds: oxides, hydroxides, carbonates, hydrocarbonates, phosphates, silicates, borates, formates, acetates, and the salts of higher organic acids (soaps).

British Patent 708,744 by Kolbel et al. describes a method of alkalization of an iron-based Fischer-Tropsch catalyst in a packed bed reactor to maintain its wax-forming capability. In the described method, alkali metal compound is added to an extraction agent which is used for the periodic extraction of paraffin wax from the catalyst. In the preferred mode of operation, the alkali metal compound is added to the extraction agent after the bulk of the wax has been extracted. Suitable inorganic alkali metal compounds are identified in the patent as the oxides, hydroxides, carbonates, bicarbonates, phosphates, silicates, and borates of sodium and potassium. Also mentioned as being suitable are organic alkali metal compounds such as alcoholates, formates, acetates, or the alkali metal salts of higher organic acids. The patent states that the alkali metal compound, unless it is soluble in the extraction agent, must be finely ground and able to form a stable suspension in the extraction agent.

Frame and Gala (Proceedings of the U.S. Department of Energy Contractors Review Meeting, pp. 911–942, September 1993) presented the results of a laboratory investigation into the alkalization of an iron-based Fischer-Tropsch catalyst in a slurry reactor. Alkalization was done using potassium laureate $(CH_3(CH_2)_{10}CO_2—K^+)$ which is soluble in the hydrocarbon oil reaction medium. Alkalization was done at the start of CO hydrogenation or during an experimental run.

SUMMARY OF THE INVENTION

The present invention is a process for the synthesis of a $C_2+$ aliphatic alcohol from hydrogen and carbon oxides in the presence of a copper-based catalyst which has been impregnated with an alkali metal compound. The process differs from the prior art in that the catalyst is impregnated with the alkali metal compound in the same slurry reactor which is used for reacting the hydrogen and carbon oxides. By contrast, in the prior art $C_2+$ aliphatic alcohol synthesis, impregnation of the copper-based catalyst with the alkali metal compound is accomplished by a separate step in a separate vessel. By eliminating this separate step, the present invention realizes a savings in processing and equipment costs.

DETAILED DESCRIPTION OF THE INVENTION

The present invention is a process for the synthesis of a $C_2+$ aliphatic alcohol comprising the steps of:

(a) an in-situ catalyst impregnation step wherein an alkali metal compound is added to a slurry reactor containing a copper-based catalyst and an inert reaction liquid; and (b) a synthesis step wherein gaseous hydrogen and gaseous carbon oxides are reacted in the slurry reactor to form the $C_2+$ aliphatic alcohol.

A key to the present invention is that the copper-based catalyst is impregnated with the alkali metal compound in the same slurry reactor that is used for reacting the hydrogen and carbon oxides. Heretofore, alkali impregnation of the copper-based catalyst for $C_2+$ aliphatic alcohol. synthesis was performed by a separate impregnation step in a separate vessel.

It should be noted that effective impregnation of the copper-based catalyst can be done regardless of whether the alkali metal compound is soluble or insoluble in the inert reaction liquid. After the impregnation step and prior to the synthesis step, the copper-based catalyst (in which the copper may be present in an oxidation state greater than zero) is converted to the active form by reducing the copper to substantially zero-valent copper by introducing a reducing gas into the slurry reactor.

In a preferred embodiment of the present invention, the $C_2+$ aliphatic alcohol is isobutanol; the alkali metal in the alkali metal compound is cesium; and the inert reaction liquid is a hydrocarbon-based oil.

The process of the present invention will now be illustrated by the following Examples. As demonstrated in these Examples, the isobutanol product yield for the present invention is essentially the same as compared to where the catalyst is prepared by conventional impregnation outside of the slurry reactor. This is a surprising and unexpected result.

EXAMPLE 1

This example describes a typical reaction test procedure and presents results obtained for a $Cu/ZnO/Al_2O_3$ catalyst without alkali impregnation.

The catalyst used was a commercially available methanol synthesis catalyst in the powder form. This catalyst was placed, together with mineral oil, into a 50 cc stirred autoclave reactor. The reactor was set up to run like a continuous stirred tank reactor (CSTR). Reactor pressure was maintained by a back pressure regulator and reactor exit gas flow rate was measured using a wet test meter. The products of the reaction of synthesis gas were obtained as a vapor, since the flow lines downstream from the reactor were heat-traced. Analysis of reaction products and unconverted feed gas was done by on-line gas chromatography.

For test 12071-98, 4.25 g of catalyst was used with 20.0 g of mineral oil. For test 13464-01, which is a repeat run, 6.0 g of catalyst was used with 20.3 g of oil. The catalyst was reduced using a feed gas consisting of $CO/H_2/CO_2/N_2$ in 2.1/1/4/0.5/96 molar proportions at a pressure of 7.8 atm. During reduction, the reactor temperature was slowly increased from room temperature to 240° C. The feed gas was then changed to a $CO/H_2/CO_2/N_2$ mixture of 66.30/3/1 molar proportions and the reactor was pressurized to 59 atm. The feed rate was adjusted to 5,000 std. lit. per kg of catalyst per hr and the temperature raised to 300° C. This condition was maintained for approximately 20 hr before analysis of the product stream was done. Table 1 shows the measured synthesis rates for the major products for the two runs on this catalyst.

TABLE 1

| | Production Rate (g/kg of catalyst/hr) | |
|---|---|---|
| | Test No. 12071–98 | Test No. 13465–01 |
| methanol | 215 | 225 |
| ethanol | 11.8 | 11.3 |
| 1-propanol | 6.6 | 6.8 |
| isobutanol | 15.1 | 13.4 |
| 1-butanol | 3.1 | 2.8 |
| 2-methyl-1-butanol | 7.3 | 6.5 |
| 1-pentanol | 1.4 | 1.3 |
| 2-methyl-1-pentanol | 4.9 | 4.5 |
| 1-hexanol | 1.9 | 1.6 |
| dimethyl ether | 2.8 | 1.9 |
| methyl acetate | 3.9 | 3.8 |
| C1–C6 paraffins | 15.0 | 16.5 |

EXAMPLE 2

A series of cesium-promoted $Cu/ZnO/Al_2O_3$ catalysts, containing various quantities of cesium, were prepared by the incipient wetness method. The substrate was the same commercial methanol synthesis catalyst that was used in Example 1.

The following procedure was used in the preparation of these catalysts. The desired quantity of $Cu/ZnO/Al_2O_3$ catalyst was weighed out. A quantity of deionized water of sufficient quantity that, if added to the $Cu/ZnO/Al_2O_3$ catalyst, a thick paste would be formed. The desired amount of cesium formate ($CsOOCH \cdot xH_2O$, FW=191.73) crystals were then dissolved in the water. The quantities of $Cu/ZnO/Al_2O_3$ catalyst, cesium formate crystals, and water used for preparation, along with the calculated amount of cesium per unit weight of $Cu/ZnO/Al_2O_3$, is shown in Table 2.

For the preparation of each catalyst, the cesium formate solution was added dropwise to the $Cu/ZnO/Al_2O_3$ catalyst while the mixture was continuously stirred to ensure uniform distribution of the solution onto the powder. After adding the entire solution, at which time a thick paste was formed, the paste was allowed to dry at room temperature for 16 hr. It was then further dried at 120° C. for 1 hr in air and calcined at 350° C. for 2 hr in air in a forced-convection oven.

Each catalyst was tested in accordance with the procedure outlined in Example 1. Catalyst No. 12071-89-A was tested twice. Tables 3A and 3B show the measured synthesis rates for the major products. As shown in these tables, the rate of synthesis of isobutanol goes through a maximum with increasing Cs loading. Five of the Cs containing catalysts produce more isobutanol than the unpromoted $Cu/ZnO/Al_2O_3$ catalyst substrate. These catalysts contain Cs in the range of 5.2E-5 to 15.6E-5 gmole of Cs per g of $Cu/ZnO/Al_2O_3$.

TABLE 3A

| | Production Rate (g/kg of catalyst/hr) | | | |
|---|---|---|---|---|
| | Catalyst 12071-88-A Test No. 12071-91 | Catalyst 12071-89-A Test No. 12200-57 | Catalyst 12071-89-A Test No. 12432-04 | Catalyst 12071-69-1 Test No. 12200-48 |
| methanol | 179 | 194 | 207 | 211 |
| ethanol | 10.7 | 11.6 | 12.6 | 11.7 |
| 1-propanol | 6.9 | 8.7 | 9.5 | 10.7 |
| isobutanol | 15.2 | 20.5 | 21.2 | 25.1 |
| 1-butanol | 3.1 | 3.4 | 3.7 | 3.6 |
| 2-methyl-1-butanol | 7.0 | 8.2 | 8.6 | 8.4 |
| 1-pentanol | 1.4 | 1.6 | 1.9 | 1.9 |
| 2-methyl-1-pentanol | 5.0 | 6.4 | 6.7 | 7.0 |
| 1-hexanol | 1.7 | 2.0 | 2.2 | 2.3 |
| dimethyl ether | 1.5 | 1.3 | 1.3 | 1.1 |
| methyl acetate | 3.5 | 3.6 | 3.9 | 3.5 |
| C1–C6 paraffins | 13.9 | 13.7 | 13.7 | 12.2 |

TABLE 2

| | Quantities Used in Preparation | | | | |
|---|---|---|---|---|---|
| Catalyst No. | $Cu/ZnO/Al_2O_3$ (g) | CsOOCH (g) | $H_2O$ (g) | g of Cs per g of $Cu/ZnO/Al_2O_3$ | gmole of Cs per g of $Cu/ZnO/Al_2O_3$ |
| 12071-88-A | 30.0 | 0.151 | 25.0 | 0.00348 | 2.625E-05 |
| 12071-89-A | 30.0 | 0.300 | 25.1 | 0.00693 | 5.215E-05 |
| 12071-69-1 | 60.0 | 0.969 | 44.0 | 0.01119 | 8.423E-05 |
| 12071-91-A | 30.0 | 0.601 | 25.0 | 0.01388 | 1.044E-04 |
| 12071-98-A | 30.0 | 0.750 | 25.1 | 0.01732 | 1.303E-04 |
| 12071-92-A | 30.0 | 0.900 | 25.0 | 0.02078 | 1.564E-04 |
| 12071-99-A | 30.0 | 1.210 | 25.0 | 0.02795 | 2.103E-04 |

TABLE 3B

|  | Production Rate (g/kg of catalyst/hr) | | | |
| --- | --- | --- | --- | --- |
|  | Catalyst 12071-91-A Test No. 12071-95 | Catalyst 12071-98-A Test No. 12200-62 | Catalyst 12071-92-A Test No. 12200-60 | Catalyst 12071-99-A Test No. 12200-64 |
| methanol | 199 | 214 | 208 | 200 |
| ethanol | 10.6 | 10.2 | 8.3 | 5.7 |
| 1-propanol | 12.2 | 13.3 | 13.8 | 11.7 |
| isobutanol | 26.0 | 28.2 | 21.3 | 10.1 |
| 1-butanol | 3.5 | 3.4 | 2.7 | 1.5 |
| 2-methyl-1-butanol | 8.0 | 7.6 | 4.9 | 2.4 |
| 1-pentanol | 1.9 | 1.9 | 1.6 | 1.0 |
| 2-methyl-1-pentanol | 6.6 | 6.2 | 4.1 | 2.2 |
| 1-hexanol | 2.0 | 1.8 | 1.4 | 1.3 |
| dimethyl ether | 0.9 | 0.9 | 0.8 | 0.5 |
| methyl acetate | 2.9 | 2.8 | 2.0 | 1.0 |
| C1–C6 paraffins | 7.1 | 8.1 | 4.9 | 4.7 |

EXAMPLE 3

A potassium-promoted $Cu/ZnO/Al_2O_3$ catalyst (Catalyst No. 13040-59) was prepared by the incipient wetness impregnation technique. The same $Cu/ZnO/Al_2O_3$ catalyst that was used in Examples 1 and 2 was doped with an aqueous solution of potassium hydroxide (KOH) using the following procedure. First, 30.0 g of $Cu/ZnO/Al_2O_3$ catalyst and 23 g of deionized water were weighed out. Then 0.308 g of KOH (containing approximately 12.5 wt % bound $H_2O$) was weighed out and dissolved in the deionized water. The solution was then added dropwise to the $Cu/ZnO/Al_2O_3$ catalyst powder with continuous stirring to ensure uniform coverage of the powder. When all of the solution had been added, the mixture was the consistency of a thick paste. Drying and calcination was done as described in Example 2 for the Cs-promoted catalysts, except the room temperature air-dry was done for 72 hr. This catalyst contains 16.0E-5 gmole of K per g of $Cu/ZnO/Al_2O_3$.

Testing of catalyst 13040-59 was done in accordance with the procedure described in Example 1. The synthesis rates for the major products are shown in Table 4. The isobutanol rate for this catalyst is significantly higher than that for the substrate (see Example 1).

TABLE 4

|  | Production Rate (g/kg of catalyst/hr) Test No. 13019-91 |
| --- | --- |
| methanol | 241 |
| ethanol | 8.4 |
| 1-propanol | 10.0 |
| isobutanol | 19.2 |
| 1-butanol | 2.3 |
| 2-methyl-1-butanol | 5.4 |
| 1-pentanol | 1.3 |
| 2-methyl-1-pentanol | 4.4 |
| 1-hexanol | 1.2 |
| dimethyl ether | 1.0 |
| methyl acetate | 2.4 |
| C1–C6 paraffins | 6.3 |

In the following Examples 4 through 8, promotion of the $Cu/ZnO/Al_2O_3$ catalyst with alkali was done in the slurry reactor used for the conversion of synthesis gas as per the process of the present invention.

EXAMPLE 4

For run No. 13040-13, 6.0 g of $Cu/ZnO/Al_2O_3$, 0.098 g of cesium formate crystals, and 21.0. g of mineral oil were added to the autoclave reactor. The mixture contained 8.5E-5 gmole of Cs per g of $Cu/ZnO/Al_2O_3$. Reduction and testing was done in accordance with the procedure described in Example 1. The results for the test are shown in Table 5.

EXAMPLE 5

For Run No. 13019-47, 6.0 g of $Cu/ZnO/Al_2O_3$, 0.119 g of cesium formate crystals, and 20.5 g of mineral oil were added to the autoclave reactor. The mixture contained 10.3E-5 gmole of Cs per g of $Cu/ZnO/Al_2O_3$. Reduction and testing was done in accordance with the procedure described in Example 1. The results for the test are shown in Table 5.

EXAMPLE 6

In this example, the cesium formate crystals were first dissolved in methanol. For Run No. 13040-15 g of $Cu/ZnO/Al_2O_3$, 0.119 g of cesium formate crystals dissolved in 5.04 g of methanol, and 20.9 g of mineral oil were added to the autoclave reactor. The mixture contained 10.3E-5 gmole of Cs per g of $Cu/ZnO/Al_2O_3$. Reduction and testing was done in accordance with the procedure described in Example 1. The results for the test are shown in Table 5.

EXAMPLE 7

In this example, a 50 wt % aqueous solution of cesium hydroxide (CsOH) was used as the cesium source. For Run No. 13019-49, 6.0 g of $Cu/ZnO/Al_2O_3$, 0.183 g of cesium hydroxide solution, and 20.2 g of mineral oil were added to the autoclave reactor. The mixture contained 10.2E-5 gmole of Cs per g of $Cu/ZnO/Al_2O_3$. Reduction and testing was done in accordance with the procedure described in Example 1. The results for the test are shown in Table 5.

EXAMPLE 8

In this example, a potassium hydroxide (KOH) was used as the alkali. For Run No. 13019-99, 6.0 g of $Cu/ZnO/Al_2O_3$, 0.062 g of KOH (12.5% bound $H_2O$), and 20.1 g of mineral oil were added to the autoclave reactor. The mixture contained 16.1E-5 gmole of K per g of $Cu/ZnO/Al_2O_3$. Reduction and testing was done in accordance with the procedure described in Example 1. The results for the test are shown in Table 5.

TABLE 5

|  | Production Rate (g/kg of catalyst/hr) | | | | |
| --- | --- | --- | --- | --- | --- |
|  | Test No. 13040-13 | Test No. 13019-47 | Test No. 13040-15 | Test No. 13019-49 | Test No. 13019-99 |
| methanol | 203 | 203 | 203 | 199 | 247 |
| ethanol | 9.1 | 7.9 | 7.5 | 7.7 | 8.0 |
| 1-propanol | 10.4 | 12.1 | 12.6 | 11.6 | 9.7 |
| isobutanol | 23.3 | 25.8 | 25.0 | 23.2 | 22.2 |
| 1-butanol | 2.8 | 2.6 | 2.5 | 2.6 | 2.2 |
| 2-methyl-1-butanol | 7.6 | 6.8 | 6.1 | 7.0 | 6.3 |

TABLE 5-continued

| | Production Rate (g/kg of catalyst/hr) | | | | |
|---|---|---|---|---|---|
| | Test No. 13040-13 | Test No. 13019-47 | Test No. 13040-15 | Test No. 13019-49 | Test No. 13019-99 |
| 1-pentanol | 1.6 | 1.6 | 1.5 | 1.6 | 1.3 |
| 2-methyl-1-pentanol | 6.6 | 5.9 | 5.0 | 5.9 | 5.4 |
| 1-hexanol | 1.7 | 1.4 | 1.3 | 1.5 | 1.3 |
| dimethyl ether | 1.1 | 0.8 | 0.8 | 0.7 | 1.1 |
| methyl acetate | 2.9 | 2.3 | 2.2 | 2.2 | 2.4 |
| C1–C6 paraffins | 10.3 | 7.1 | 6.7 | 6.8 | 7.3 |

The results of Examples 4 through 8 show that, surprisingly, the isobutanol production rate for the present invention, where alkali promotion/impregnation is done in the slurry reactor, is essentially the same as compared to where the catalyst is prepared by conventional impregnation outside of the slurry reactor.

The present invention has been described with reference to specific examples thereof. These examples should not be seen as a limitation of the scope of the present invention; the scope of such being ascertained by the following claims.

We claim:

1. A process for the synthesis of a $C_2+$ aliphatic alcohol comprising the steps of:

(a) an in-situ catalyst impregnation step wherein an alkali metal compound is added to a slurry reactor containing a copper-based catalyst and an inert reaction liquid; and (b) a synthesis step wherein gaseous hydrogen and gaseous carbon oxides are reacted in the slurry reactor to form the $C_2+$ aliphatic alcohol.

2. The process of claim 1 wherein the alkali metal compound is soluble in the inert reaction liquid.

3. The process of claim 1 wherein the alkali metal compound is insoluble in the inert reaction liquid.

4. The process of claim 1 wherein, subsequent to the impregnation step and prior to the synthesis step, the copper-based catalyst is converted to the active form by introducing a reducing gas into the slurry reactor.

5. The process of claim 1 wherein the $C_2+$ aliphatic alcohol is isobutanol; the alkali metal in the alkali metal compound is cesium; and the inert reaction liquid is a hydrocarbon-based oil.

* * * * *